United States Patent
Hecht et al.

(10) Patent No.: US 9,782,329 B2
(45) Date of Patent: Oct. 10, 2017

(54) HARDENABLE DENTAL COMPOSITION CONTAINING A MIXTURE OF AGGLOMERATED AND AGGREGATED NANO-PARTICLES, KIT OF PARTS AND USE THEREOF

(71) Applicant: 3M INNOVATIVE PROPERTIES COMPANY, St. Paul, MN (US)

(72) Inventors: Reinhold Hecht, Kaufering (DE); Uwe H. Hoheisel, Tuerkenfeld (DE); Adrian S. Eckert, Herrsching (DE); Bernhard Hofmann, Peissenberg (DE)

( * ) Notice: Subject to any disclaimer, the term of this patent is extended or adjusted under 35 U.S.C. 154(b) by 0 days.

(21) Appl. No.: 14/902,948

(22) PCT Filed: Jul. 1, 2014

(86) PCT No.: PCT/US2014/044985
§ 371 (c)(1),
(2) Date: Jan. 5, 2016

(87) PCT Pub. No.: WO2015/006087
PCT Pub. Date: Jan. 15, 2015

(65) Prior Publication Data
US 2016/0136059 A1    May 19, 2016

(30) Foreign Application Priority Data
Jul. 8, 2013  (EP) ..................... 13175512

(51) Int. Cl.
*A61K 6/083* (2006.01)
*A61K 6/00* (2006.01)
*A61K 6/09* (2006.01)

(52) U.S. Cl.
CPC ............ *A61K 6/083* (2013.01); *A61K 6/0008* (2013.01); *A61K 6/0073* (2013.01); *A61K 6/0088* (2013.01); *A61K 6/09* (2013.01)

(58) Field of Classification Search
CPC .............................. A61K 6/0073; A61K 6/083
See application file for complete search history.

(56) References Cited

U.S. PATENT DOCUMENTS

| | | |
|---|---|---|
| 3,347,954 A | 10/1967 | Bredereck |
| 3,541,068 A | 11/1970 | Taylor |
| 4,071,124 A | 1/1978 | Price |
| 4,443,587 A | 4/1984 | Schmitt |
| 4,544,742 A | 10/1985 | Schmitt |
| 4,642,126 A | 2/1987 | Zador |
| 4,652,274 A | 3/1987 | Boettcher |
| 5,569,691 A | 10/1996 | Guggenberger |
| 5,918,772 A | 7/1999 | Keller |
| 5,944,419 A | 8/1999 | Streiff |
| 6,127,449 A | 10/2000 | Bissinger |
| 6,444,725 B1 | 9/2002 | Trom |
| 6,572,693 B1 | 6/2003 | Wu |
| 6,677,393 B1 | 1/2004 | Zech |
| 6,730,156 B1 | 5/2004 | Windisch |
| 6,899,948 B2 | 5/2005 | Zhang |
| 6,936,642 B2 | 8/2005 | Lehmann |
| 8,722,759 B2 | 5/2014 | Craig |
| 2001/0047047 A1* | 11/2001 | Nowak ............... C08G 18/4816 524/430 |
| 2003/0008967 A1 | 1/2003 | Hecht |
| 2004/0110864 A1 | 6/2004 | Hecht |
| 2005/0234148 A1 | 10/2005 | Ruppert |
| 2006/0187752 A1 | 8/2006 | Keller |
| 2007/0090079 A1 | 4/2007 | Keller |
| 2007/0142495 A1* | 6/2007 | Neffgen ............... A61K 6/0017 523/116 |
| 2010/0016466 A1 | 1/2010 | Lueck |
| 2017/0036161 A1* | 2/2017 | McMurray ............. B01D 53/10 |

FOREIGN PATENT DOCUMENTS

| | | |
|---|---|---|
| CA | 2256191 | 7/1999 |
| EP | 1512724 | 3/2005 |
| EP | 2072029 | 6/2009 |
| EP | 2167013 | 3/2010 |
| WO | WO 01-30304 | 5/2001 |
| WO | WO 2007-140440 | 12/2007 |
| WO | WO 2008-014224 | 1/2008 |
| WO | WO 2009-151957 | 12/2009 |
| WO | WO 2012-057917 | 5/2012 |

OTHER PUBLICATIONS

Curtis, "The mechanical properties of nanofilled resin-based composites: The impact of dry and wet cyclic pre-loading on bi-axial flexure strength," Dental Materials, Feb. 2009, vol. 25, No. 2, pp. 188-197, XP025768197.
Misra, "Redox Polymerization," Progress in Polymer Science, 1982, vol. 8, pp. 61-131.
Rosentritt, "Regensburger Kausimulator", Apparatur zur Simulation des Kauorgans, Materialprüfung, 1997, vol. 39, No. 3, pp. 77-80.
1507 Extended EP Search Report for EP13175512.6, PCT/US2014/044985, dated Nov. 6, 2013, 7pages.
International Search Report for PCT International Application No. PCT/US2014/044985, mailed on Sep. 30, 2014, 4pages.

* cited by examiner

*Primary Examiner* — Michael Pepitone

(57) ABSTRACT

The invention relates to a dental composition comprising filler (F1) comprising aggregated nano-sized particles in an amount of from about 30 to about 70 wt. %, filler (F2) comprising agglomerated nano-sized particles in an amount from about 1 to about 20 wt. %, hardenable component (A1) being an urethane(meth)acrylate with a functionality of at least 2 and having a molecular weight from about 400 to about 3,000 g/mol,-hardenable component (A2) being a radically polymerizable (meth)acrylate with a functionality of at least 2 being different from component (A1), redox curing initiator system, the dental composition not comprising non-agglomerated nano-sized filler in an amount above about 10 wt. %, wt. % with respect to the weight of the whole composition. The dental composition is in particular useful as or for production of permanent crown and bridges, inlays, onlays and veneers.

16 Claims, No Drawings

HARDENABLE DENTAL COMPOSITION CONTAINING A MIXTURE OF AGGLOMERATED AND AGGREGATED NANO-PARTICLES, KIT OF PARTS AND USE THEREOF

CROSS-REFERENCE TO RELATED APPLICATIONS

This application is the §371 National Stage of International Application No. PCT/US2014/044985, filed Jul. 1, 2014, which claims priority to European Patent Application No. 13175512.6, filed Jul. 8, 2013.

FIELD OF THE INVENTION

The invention relates to a dental composition which is useful as dental filling material, in particular as bulkfill material or for producing long term restorations like permanent composite crown and bridges, inlays, onlays and veneers.

BACKGROUND ART

Composite materials are well known in dentistry and can be used for example as filling materials, permanent cements or temporary crown and bridge materials. Depending on indication the different composite materials can be differentiated by their respective filler contents.

Filling composites are typically highly filled materials which are characterized by good mechanical properties like low abrasion (low wear). Unfortunately due to the high filler loading these materials sometimes tend to be brittle.

Temporary crown and bridge materials have a lower filler content compared to filling composites. This often results in an improved elasticity and a higher fracture resistance, but often goes along with an increased abrasion or wear which prevents a long-term use of these materials.

Commercially available lab composite materials for the manufacturing of dental restorations such as crowns cannot be used in an in-office or chair-side procedure and require the involvement of an external dental laboratory. Alternatively composite milling blocks such as Paradigm™ MZ 100 (3M ESPE) can be used in an in-office or chairside procedure but require an investment in considerable expensive CAD/CAM technology.

Thus, there is a need for a material that combines the properties of the materials described above which can be used for an in-office or chair-side fabrication of composite crowns and bridges without the need for an investment in CAD/CAM technology.

Further, patients and dentists nowadays have an increasing demand for long-lasting dental restorations.

EP 2 167 013 A1 (3M) relates to dental compositions containing a polyfunctional (meth)acrylate comprising urethane, urea or amide groups, methods of production and use thereof.

US 2005/0234148 A1 (Heraeus) describes agglomerated inorganic fillers for dental materials consisting of 0.5 to 50 μm agglomerates of 200 to 7000 nm inorganic particles, which are fused at their interfaces to at least one adjacent particle. WO 2012/057917 A1 (3M) describes a preformed semi-finished dental article comprising an uncured dental restoration composition comprising a certain resin system at least 50 wt.-% of nanocluster filler, wherein the uncured dental restoration composition has a first shape that is sufficiently malleable to be formed into a second shape.

U.S. Pat. No. 6,730,156 B1 (Windisch et al.) relates to a filler comprising a substantially amorphous cluster comprising non-heavy oxide particles and heavy metal oxide. The filler can be mixed into a hardenable resin to provide radiopaque dental materials having desirable strength and aesthetic character.

DESCRIPTION OF THE INVENTION

In particular, it would be desirable to have a dental composition available with high fracture resistance, low wear and sufficient flexibility. If possible, the dental composition should also be easy to apply. Ideally, the dental composition should also be aesthetically acceptable.

This objective can be achieved with the dental composition described in the present text.

In one embodiment the present invention features a dental composition comprising:
- filler (F1) comprising aggregated nano-sized particles in an amount of from about 30 to about 70 wt. %,
- filler (F2) comprising agglomerated nano-sized particles in an amount from about 1 to about 20 wt. %,
- hardenable component (A1) being an urethane(meth)acrylate with a functionality of at least 2 and having a molecular weight above about 450 g/mol,
- hardenable component (A2) being a radically polymerizable (meth)acrylate with a functionality of at least 2 being different from component (A1),
- redox initiator system or dark curing initiator system.

The dental composition does typically not comprise non-agglomerated nano-sized filler (e.g. average particle size below about 50 nm) in an amount above about 10 wt. %.

The invention is also related to a kit of parts comprising the dental composition as described in the present text and at least of or all of the following parts:
- means for mixing,
- dental impression material,
- dental cement.

The invention is also related to the use of the dental composition described in the present text as or for producing crown(s) bridge(s), inlay(s), onlay(s), veneer(s) and as bulk-fill material.

Definitions

Unless defined differently, for this description the following terms shall have the given meaning:

A "dental composition" or a "composition for dental use" or a "composition to be used in the dental field" is any composition which can be used in the dental field. In this respect the composition should be not detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges. A "hardenable component or material" or "polymerizable component" is any component which can be cured or solidified e.g. by heating to cause polymerization, chemical crosslinking, radiation-induced polymerization or crosslinking by using a redox initiator. A hardenable component may contain only one, two, three or more polymerizable groups. Typical examples of polymerizable groups include unsaturated carbon groups, such as a vinyl group being present i.a. in a (methyl)acrylate group. An "initiator" is a substance being able to start or initiate the curing process of a hardenable composition.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth) acryloxy" group is a shorthand term referring to either an acryloxy group (i. e., $CH_2=CH-C(O)-O-$) and/or a methacryloxy group (i. e., $CH_2=C(CH_3)-C(O)-O-$).

A "curing, hardening or setting reaction" is used interchangeable and refers to a reaction wherein physical properties such as viscosity and hardness of a composition changes over the time due to a chemical reaction between the individual components.

An "polymerizable component comprising an acidic group" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues such as C—P(O)(OH)OH, sulfonic acid residues, such as —$SO_3H$ or sulfinic acid residues such as —$SO_2H$.

A "powder" means a dry, bulk solid composed of a large number of very fine particles that may flow freely when shaken or tilted.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

A "nano-sized filler" is a filler, the individual particles thereof have a size in the region of nanometers, e.g. an average particle diameter of less than about 200 nm or less than about 100 nm or less than about 50 nm. Useful examples are given in U.S. Pat. No. 6,899,948 and U.S. Pat. No. 6,572,693, the content of which especially with regard to nano-sized silica particles is herein incorporated by reference.

The measurement of the size of nano-particles is preferably based on a TEM (transmission electron microscopy) method, whereby a population is analyzed to obtain an average particle diameter. A preferred method for measuring the particle diameter can be described as follows:

Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 KV. A population size of about 50-100 particles can be measured and an average diameter is determined.

"Agglomerated" is descriptive of a weak association of particles usually held together by charge or polarity and can be broken down into smaller entities. The specific surface of agglomerated particles does not essentially deviate from the specific surface of the primary particles the agglomerate is made of (cf. DIN 53206; 1972).

Agglomerated fillers are commercially available e.g. from Degussa, Cabot Corp or Wacker under the product designation Aerosil™, CAB—O-SIL™ and HDK.

A "non-agglomerated filler" means that the filler particles are present in the resin in a discrete, un-associated (i.e. non-agglomerated and non-aggregated) stage. If desired this can be proven by TEM microscopy.

Non-agglomerated nano-sized silicas are commercially available e.g. from Nalco Chemical Co. (Naperville, Ill.) under the product designation NALCO COLLOIDAL SILICAS e.g. NALCO products #1040, 1042, 1050, 1060, 2327 and 2329. Non-agglomerated fillers are used and described e.g. in EP 2 167 013 B1 (3M). The content of this reference is herewith incorporated by reference.

"Aggregated," as used herein, is descriptive of a strong association of particles often bound together by, for example, residual chemicals treatment or partially sintering. The specific surface of aggregated particles is typically smaller than the specific surface of the primary particles the aggregate is made of (cf. DIN 53206; 1972).

Further breakdown of the aggregates into smaller entities may occur during a polishing step applied to the surface of a composition containing the aggregated filler but not during dispersing the aggregated particles in a resin.

Aggregated fillers and processes for the production and surface treatment thereof are described e.g. in WO 01/30304 and U.S. Pat. No. 6,730,156 (3M).The content of these references is herewith incorporated by reference.

"Dispersed within the resin" means that filler particles are present in the resin as agglomerated or aggregated or discrete (i.e., un-associated, non-agglomerated and non-aggregated) particles.

An "urethane group" is a group having the structure "—NH—CO—O—".

An "urea group" is a group having the structure "—NH—CO—NH—".

An "amide group" is a group having the structure "—NH—CO—".

A "unit" is a single building block of a chemical molecule or substructure thereof Single units are connected to each other. Typical units include: $CH_3-$, $-CH_2-$, $-O-$, $-S-$, $-NR^1-$, $-CO-$, $-CR^1=$, $$-\overset{|}{\underset{|}{C}}-,\quad -\overset{|}{\underset{|}{C}}-R1,\quad \overset{\diagdown}{\diagup}C=,\quad \overset{\diagdown}{\diagup}C=N-,\quad \overset{|}{\underset{\diagdown}{\diagup}}N\diagdown,$$

$-N=$, $-CR^1R^2-$, with $R^1$ and $R^2$ independently selected from hydrogen, linear alkyl groups (including C1, C2, C3, C4, C5 C6 groups), substituted alkyl groups (including C1, C2, C3, C4, C5 C6 groups), alkenyl groups (including C1, C2, C3, C4, C5 C6 groups), cycloalkyl groups (including C4 to C14 groups), substituted cycloalkyl groups (including C4 to C14 groups), arylalkyl groups (including C7 to C20), aryl groups (including C6 to C14) or substituted aryl groups (including C7 to C20). These units can form linear, branched or cyclic structures such as alkyl, cycloalkyl, aryl, ester, urethane or amide groups.

A "connector element" is an element acting as a center connecting the individual (meth)acrylate containing side chains. The connector element can have a cyclic or branched structure. The connector element can even be a single atom including N. If the connector element has a cyclic structure, it can be a saturated, unsaturated or aromatic homocycle, that is, it comprises only hydrocarbon or substituted hydrocarbon units, or it can be a saturated, unsaturated or aromatic heterocycle, that is, it comprises hydrocarbon or substituted hydrocarbon units and at least one hetero atom including —O—, —N=, —NH—, —NR$^1$— and/or —S—. If the connector element has a branched structure, it comprises a central atom like C or N from which at least three or four individual (meth)acrylate containing side chains are extending. Independently from the chemical structure of the connector element, the arrangement of the individual (meth)acrylate containing side chains with respect to the connector element can be symmetric or asymmetric.

A "spacergroup" is a group connecting at least two other groups in a chemically defined molecule. This group can be a substituted or not substituted carbon chain, which can in addition contain hetero atoms (including O, N and S) or functions like carbonyl groups.

A "dental impression material" is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

A "temporary crown and bridge material" is a hardenable material used for making dental crowns and bridges. These materials are typically used during the time period a dental technician needs for producing a permanent prosthetic work such as a crown or bridge. These time periods can last from a few days (1 to about 6 days), a few weeks (1 to about 4 weeks) or a few months (1 to about 6 month). A long term crown and bridge material is typically used over a time period of about 6 to 24 months.

In contrast to a long term crown and bridge material, a "permanent crown and bridge material" can be used over a time period of more than 2 years and especially more than 5 years. The term "visible light" is used to refer to light having a wavelength of about 400 to about 800 nanometers (nm).

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.). Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

DETAILED DESCRIPTION OF THE INVENTION

It has been found that the composition described in the present text fulfils the practitioners' needs especially with regard to the balance of properties like high abrasion resistance (i.e. low wear), sufficient flexibility and high fracture resistance. The combination of different fillers in certain amounts combined with a certain resin matrix enables the provision of a composition having on the one hand a high filler load and on the other hand good handling properties combined with well-balanced physical properties.

This is usually difficult to achieve. A high filler load typically goes along with difficult mixing properties and an insufficient flexibility of the hardened composition. On the other hand, a low filler load typically facilitates the mixing and may contribute to a better flexibility, but usually results in an insufficient abrasion resistance.

Due to its viscosity properties, the composition is also easy to apply as it can be mixed and dispensed from known mixing and dispensing systems. If desired, this can be verified with an extrusion test as described in more detail below. The composition described in the present text enables the practitioner to provide the patient with a dental restoration which can be used for a longer period of time compared to existing temporary or long-term crown and bridge materials. The composition cannot only be used for producing long-term crown and bridges but also inlays, onlays and veneers on composite basis. Also the use as a bulk-fill material is possible.

Further, the dental restoration can be produced chair-side, i.e. without involving a dental laboratory. There is also no need to invest in an expensive CAD/CAM technology. The dental composition described in the present text comprises at least two kind of fillers, filler (F1) and filler (F2). The dental composition is characterized by a comparable high filler load. For comparison, the filler load of typical temporary crown and bridge materials is in the range from about 30 to about 40 wt. % with respect to the weight of the whole composition. It was found that a high filler load is beneficial to increase the wear resistance, thus enabling the provision of a dental material which can be used for a long term in the mouth of a patient. Filler (F1) comprises aggregated nano-sized particles. The chemical nature of filler (F1) is not particularly limited unless the intended purpose cannot be achieved.

According to one embodiment, filler (F1) can be characterized by at least one or all of the following features:

Specific surface: from about 50 to about 400 or from 60 to about 300 or from 80 to about 250 m$^2$/g, comprising particles of SiO$_2$, ZrO$_2$ and mixtures thereof. If desired, the specific surface can be determined according to Brunauer, Emmet and Teller (BET) by using a device (Monosorb) available from Quantachrome.

If desired, the mean particle size can be determined by light scattering using e.g. a Malvern Mastersizer 2000 device available from Malvern Instruments. Filler (F1) can be produced according to the processes described e.g. in WO 01/30304 or U.S. Pat. No. 6,730,156.

Filler (F1) can be prepared from a suitable sol and one or more oxygen containing heavy metal compound solution(s) precursors which may be salts, sols, solutions, or nano-sized particles; of these, sols are preferred. For purposes of this invention, a sol is defined as a stable dispersion of colloidal solid particles within a liquid. The solid particles are typically denser than the surrounding liquid and small enough so that the dispersion forces are greater than the gravitational force. In addition, the particles are of a size small enough so that they generally do not refract visible light. Judicious choice of the precursor sols leads to desired degree of visual opacity, strength etc. Factors that will guide the choice of the sol depends on the combination of the following properties: a) the average size of the individual particles, which is preferably less than about 100 nm in diameter, b) the acidity: the pH of the sol should be preferably be below about 6 and more preferably below about 4, and c) the sol should be free of impurities that cause undue aggregation (during the filler preparation process) of the individual discrete particles, during the subsequent steps such as spray drying or calcining, into larger size particles that cannot be easily dispersed or commuted and hence decrease the translucency and polishability.

If the starting sol is basic, it should be acidified e.g. by addition of nitric or other suitable acid to decrease the pH. However choosing a basic starting sol is less desirable since it requires an additional step and may lead to the introduction of undesired impurities. Typical impurities that are preferably avoided are metal salts, particularly salts of alkaline metals e.g. sodium.

The non-heavy metal sol and heavy metal oxide precursors are mixed together preferably at a molar ratio to match the index of refraction of the hardenable resin. This imparts a low and desirable visual opacity. Preferably, the molar ratio ranges of non-heavy metal oxide ("non-HMO") to heavy metal oxide ("HMO"), expressed as non-HMO:HMO is about 0.5:1 to about 10:1, more preferably about 3:1 to about 9:1, and most preferable about 4:1 to 7:1.

In a preferred embodiment where the aggregated nano-sized particles contain silica and zirconium containing compounds, the method of preparation starts with a mixture of silica sol and zirconyl acetate, at about a 5.5:1 molar ratio.

Prior to mixing the non-heavy metal oxide sol with the heavy metal oxide precursor, the pH of the non-heavy metal oxide sol is preferably reduced to provide an acidic solution having a pH of about 1.5 to about 4.0. The non-heavy metal oxide sol is then slowly mixed with the solution containing the heavy metal oxide precursor and vigorously agitated. Strong agitation is preferably performed throughout the blending process. The solution is then dried to remove the water and other volatile components. Drying can be accomplished in various ways, including for example, tray drying, fluidized bed and spray drying. In the preferred method where zirconyl acetate is used, drying by means of spray drying.

The resulting dried material is preferably made up of small substantially spherical particles as well as broken hollow spheres. These fragments are then batch calcined to further remove residual organics. The removal of the residual organics allows the filler to become more brittle, which results in more efficient particle size reduction. During calcining, the soak temperature is preferably set at about 200° C. to about 800° C., more preferably about 300° C. to about 600° C. Soaking is performed for about 0.5 hours to about 8 hours, depending on the amount of material being calcined. It is preferred that the soak time of the calcine step be such that a plateaued surface area is obtained. It is preferred that the time and temperature be chosen such that the resulting filler is white in color, free from black, grey, or amber colored particles, as determined by visual inspection.

The calcined material is then preferably milled to a median particle size of less than about 5 μm, preferably less than 2 μm (on a volumetric basis), as can be determined by using a Sedigraph 5100 (Micrometrics, Norcross, Ga.). The particle size determination can be performed by first obtaining the specific density of the filler using an Accuracy 1330 Pycometer (Micrometrics, Norcross, Ga.). Milling can be accomplished by various methods including for example, stirred milling, vibratory milling, fluid energy milling, jet milling and ball milling. Ball milling is the preferred method.

The resulting fillers comprise, contain, consist essentially or consist of aggregated nano-sized particles. If desired, this can be proven by transmission electron microscopy (TEM). The surface of the particles of filler (F1) can be surface treated. The surface-treatment can be accomplished in the same manner as described in more detail for the particles of filler (F2) below or according to a process as described in U.S. Pat. No. 6,730,156 or WO 01/30304.

Once dispersed in the resin, the filler (F1) remains in an aggregated stage. That is, during the dispersion step the particles do not break up into discrete (i.e. individual) and un-associated (i.e. non-agglomerated, non-aggregated) particles. Filler (F1) is typically present in an amount of at least about 30 or at least about 35 or at least about 40 wt. % with respect to the weight of the whole composition. Filler (F1) is typically present in an amount of utmost about 70 or utmost about 60 or utmost about 50 wt. % with respect to the weight of the whole composition. Thus, filler (F1) is typically present in an amount from about 30 to about 70 or from about 35 to about 60 or from about 40 to about 50 wt. % with respect to the weight of the whole composition.

The dental composition may contain only one kind of filler (F1) or more kinds of filler (F1), e.g. two, three or four different kinds Without wishing to be bound to a specific theory, it is believed that filler (F1) contributes to the polishability of the dental composition described in the present text. It was found that the aggregates of the filler (F1) particles can break up during a polishing step contributing to a smooth surface and a lower light scattering compared to a rough surface. From a clinical standpoint of view this typically results in high gloss retention and color stability.

Using non-agglomerated fillers instead, like those used in the examples of EP 2 167 013 (A1), was not found to be suitable to achieve the desired abrasion resistance.

Further, using non-agglomerated filler often goes along with an increase in viscosity. A high viscosity, however, adversely affects the forces needed to mix and extrude the dental material from a manually driven dispenser. In addition, due to the high specific surface incorporating a high amount (e.g. more than about 40 wt.-%) of non-agglomerated filler into the resin matrix is often not possible.

Thus, it was found that using aggregated nano-sized fillers contributes to a better abrasion resistance of the dental composition, allows for a higher filler load in the resin matrix of the dental composition, facilitates the production of pastes due to better wettability properties of the filler and contributes to better handling properties.

The dental composition may contain only one kind of filler (F2) or more kinds of filler (F2), e.g. two, three or four different kinds Filler (F2) comprises agglomerated nano-sized particles. The chemical nature of filler (F2) is not particularly limited unless the intended purpose cannot be achieved. The size of the filler particles should be such that a homogeneous mixture with the hardenable component (A1) forming the hardenable resin matrix can be obtained.

According to one embodiment, filler (F2) can be characterized by at least one or all of the following features:
  Specific surface of the agglomerated nano-sized particles (BET according to Brunauer, Emmet and Teller): from about 30 to about 400 or from 50 to about 300 or from 70 to about 250 m$^2$/g;
  comprising particles of $SiO_2$, $ZrO_2$, $Al_2O_3$ and mixtures thereof.

If desired, the specific surface can be determined as described above.

Suitable agglomerated nanoparticles include fumed silicas such as products sold under the tradename Aerosil™ e.g. Aerosil OX-130, -150, and -200, Aerosil R8200 available from Degussa AG, (Hanau, Germany), CAB-O-SIL™ M5 available from Cabot Corp (Tuscola, Ill.), and HDK™, e.g. HDK-H 2000, HDK H15; HDK H18, HDK H20 and HDK H30 available from Wacker.

The surface of the filler particles of filler (F2) can be treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174 from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, cycloalkyl, hydroxy alkyl, aryl, hydroxy aryl, or amino alkyl functional silanes.

Without wishing to be bound to a specific theory, it is believed that filler (F2) contributes to the rheological behaviour of the dental composition described in the present text. Using this kind of filler enables one to provide a highly filled dental composition which nevertheless is still mixable using static mixing tips. From a clinical standpoint of view this typically results in improved handling properties such as easy mixing of the pastes and low extrusion forces from cartridge systems. Filler (F2) is typically present in an amount of at least about 1 or at least about 3 or at least about 5 wt. % with respect to the weight of the whole composition. Filler (F2) is typically present in an amount of utmost about 20 or utmost about 15 or utmost about 10 wt. % with respect to the weight of the whole composition. Thus, filler (F2) is typically present in an amount from about 1 to about 20 or from about 3 to about 15 or from about 5 to about 10 wt. % with respect to the weight of the whole composition.

The dental composition described in the present text comprises at least two kind of hardenable components, component (A1) and component (A2). Component (A1) and component (A2) are components of the resin matrix of the dark curable dental composition. The dental composition comprises at least one hardenable component (A1) being an urethane(meth)acrylate with a functionality of at least 2.

If desired, the dental composition may comprise at least two, three or four different kinds of hardenable component (A1). The molecular weight of hardenable component (A1) is at least about 450 or at least about 800 or at least about 1,000. Useful ranges include from about 450 to about 3,000 or from about 800 to about 2,700 or from about 1,000 to about 2,500. Molecules having a molecular weight above about 450 g/mol or above about 1000 g/mol are usually less volatile than molecules having a lower molecular weight and thus may contribute to providing a biocompatible composition.

Further, if the molecular weight is not sufficiently high, the desired fracture resistance of the hardended dental composition may not be achieved.

The urethane (meth)acrylates employed in the composition described in the present text are typically formed by reacting an NCO-terminated compound with a suitable monofunctional (meth)acrylate monomer such as hydroxyethyl acrylate, hydroxyethyl methacrylate, hydroxypropylmethacrylate, preferably hydroxyethyl- and hydroxypropylmethacrylate.

Urethane (meth)acrylates may be obtained by a number of processes known to the skilled person. For example, a polyisocyanate and a polyol may be reacted to form an isocyanate-terminated urethane prepolymer that is subsequently reacted with a (meth)acrylate such as 2-hydroxy ethyl(meth)acrylate. These types of reactions may be conducted at room temperature or higher temperature, optionally in the presence of catalysts such as tin catalysts, tertiary amines and the like.

Polyisocyanates which can be employed to form isocyanate-functional urethane prepolymers can be any organic isocyanate having at least two free isocyanate groups. Included are aliphatic cycloaliphatic, aromatic and araliphatic isocyanates.

Any of the known polyisocyanates such as alkyl and alkylene polyisocyanates, cycloalkyl and cycloalkylene polyisocyanates, and combinations such as alkylene and cycloalkylene polyisocyanates can be employed.

Preferably, diisocyanates having the formula X(NCO)2 are used, with X representing an aliphatic hydrocarbon radical with 2 to 12 C atoms, a cycloaliphatic hydrocarbon radical with 5 to 18 C atoms, an aromatic hydrocarbon radical with 6 to 16 C atoms and/or an araliphatic hydrocarbon radical with 7 to 15 C atoms.

Examples of suitable polyisocyanates include 2,2,4-trimethylhexamethylene-1,6-diisocyanate, hexamethylene-1,6-diisocyanate (HDI), cyclohexyl-1,4-diisocyanate, 4,4'methylene-bis(cyclohexyl isocyanate), 1,1'-methylenebis(4-isocyanato) cyclohexane, isophorone diisocyanate, 4,4'-methylene diphenyl diisocyanate, 1,4-tetramethylene diisocycanate, meta- and para-tetramethylxylene diisocycanate, 1,4-phenylene diisocycanate, 2,6- and 2,4-toluene diisocycanate, 1,5-naphthylene diisocycanate, 2,4' and 4,4'-diphenylmethane diisocycanate and mixtures thereof.

It is also possible to use higher-functional polyisocyanates known from polyurethane chemistry or else modified polyisocyanates, for example containing carbodiimide groups, allophanate groups, isocyanurate groups and/or biuret groups. Particularly preferred isocyanates are isophorone diisocyanate, 2,4,4-trimethyl-hexamethylene diisocyanate and higher-functional polyisocyanates with isocyanurate structure.

The isocyanate terminated urethane compound is capped with a (meth)acrylate to produce a urethane (meth)acrylate compound. In general, any (meth)acrylate-type capping agent having a terminal hydroxyl group and also having an acrylic or methacrylic moiety can be employed, with the methacrylic moiety being preferred.

Examples of suitable capping agents include 2-hydroxyethyl(meth)acrylate, 2-hydroxypropyl (meth)acrylate, glycerol di(meth)acrylate and/or trimethylolpropane di(meth) acrylate. Particularly preferred are 2-hydroxyethyl methacrylate (HEMA) and/or 2-hydroxyethyl acrylate (HEA).

The equivalence ratio of isocyanate groups to compounds reactive vis-à-vis isocyanate groups is 1.1:1 to 8:1, preferably 1.5:1 to 4:1. The isocyanate polyaddition reaction can take place in the presence of catalysts known from polyurethane chemistry, for example organotin compounds such as dibutyltin dilaurate or amine catalysts such as diazabicyclo [2.2.2]octane. Furthermore, the synthesis can take place both in the melt or in a suitable solvent which can be added before or during the prepolymer preparation. Suitable solvents are for example acetone, 2-butanone, tetrahydrofurane, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

Suitable examples of urethane (meth)acrylates include 7,7,9-trimethyl-4,13-dioxo-3,14-dioxa-5,12-diazahexadecane-1,16-dioxy-dimethacrylate (e.g. Plex 666-1, Röhm), 7,7,9-trimethyl-4,13-dioxo-5,12-diazahexadecane-1,16-dioxy-dimethacrylate (UDMA), urethane (methacrylates) derived from 1,4 and 1,3-Bis(1-isocyanato-1-methylethyl) bezene (e.g. as described in EP 0934926 A1) and mixtures thereof.

According to one embodiment, hardenable component (A1) can be characterized as follows:
having the structure $A\text{-}(\text{-}S1\text{-}U\text{-}S2\text{-}MA)_n$, with
A being a connector element comprising at least one unit,
S1 being a spacergroup comprising at least 4 units connected with each other,
S2 being a spacergroup comprising at least 4 units connected with each other,
the units of A, S1 and S2 being independently selected from $CH_3-$, $-CH_2-$, $-O-$, $-S-$, $-NR^1-$, $-CO-$, $-CR^1=$,

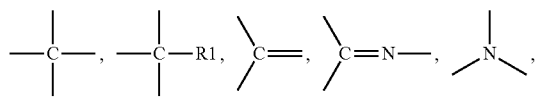

$-N=$, $-CR^1R^2-$, with $R^1$ and $R^2$ independently selected from hydrogen, alkyl, substituted alkyl, alkenyl, cycloalkyl, substituted cycloalkyl, arylalkyl, aryl or substituted aryl, wherein these units can form linear, branched or cyclic structures such as alkyl, cycloalkyl, aryl, ester, urethane or amide groups,
U being an urethane group connecting spacergroups S1 and S2,
MA being an acrylate or methacrylate group and
n being 3 to 6.

According to one embodiment the hardenable component (A1) of the composition can be presented by the structure

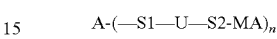

with
A being a connector element comprising at least about 1, 2, 3, 4, 5, 6, 7, 8, 9, 10, 11, 12, 13, 14, 15, 16, 17, 18, 19 or 20 units,
S1 being a spacergroup comprised of units connected with each other and comprising at least about 4, 5, 6, 7, 8, 9 or 10 units,
S2 being a spacergroup comprised of units connected with each other and comprising at least about 4, 5, 6, 7, 8, 9, 10, 12, 15, 20 or 25 units,
U being a urethane group connecting spacergroups S1 and S2,
MA being an acrylate or methacrylate group and
n being about 3 to 6 or about 4 to 6 or about 5 to 6.

It can be preferred, if A has a cyclic structure and comprises at least about 6 units.

It can further be preferred, if S1 has a linear or branched structure and comprises at least about 4 or about 6 units.

It can further be preferred, if S2 has a linear or branched structure and comprises at least about 6 or about 8 units.

A hardenable compound (A1), wherein A has a cyclic structure and comprises at least about 6 units and S1 has a linear structure and comprises at least about 4 units and S2 has a linear structure and comprises at least about 8 units and U is a urethane group can also be preferred.

Neither the atoms of the urethane group connecting S1 and S2 nor the atoms of the (meth)acrylgroup belong to the spacergroup S1 or S2. Thus, the atoms of the urethane group do not count as units of the spacergroups S1 or S2.

The nature and structure of the connector element is not particularly limited. The connector element can contain saturated (no double bonds) or unsaturated (at least one or two double bonds) units, aromatic or hetero aromatic units (aromatic structure containing atoms including N, O and S).

Specific examples of connector element A having a cyclic structure include:

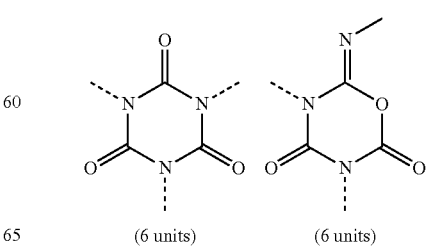

(6 units)     (6 units)

Specific examples of connector element A having a non-cyclic but branched structure include:

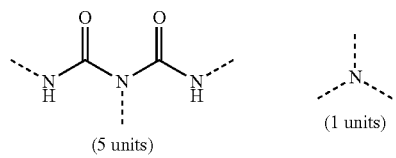

(5 units)    (1 units)

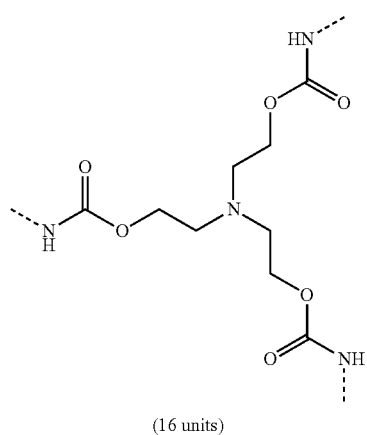

(16 units)

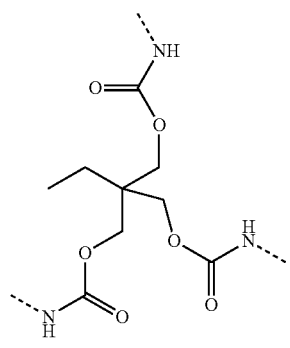

(15 units)

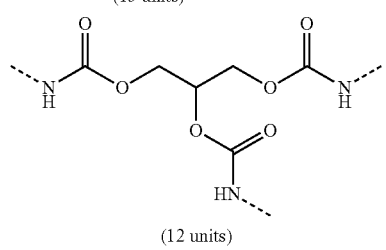

(12 units)

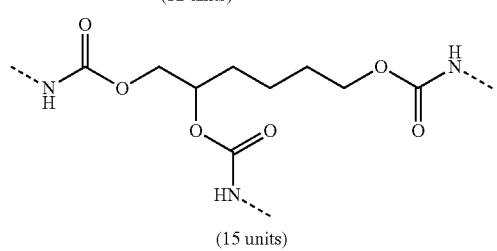

(15 units)

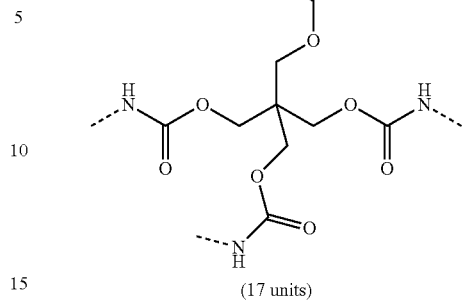

(17 units)

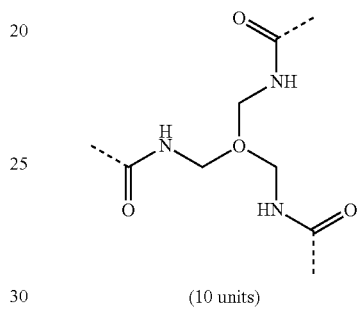

(10 units)

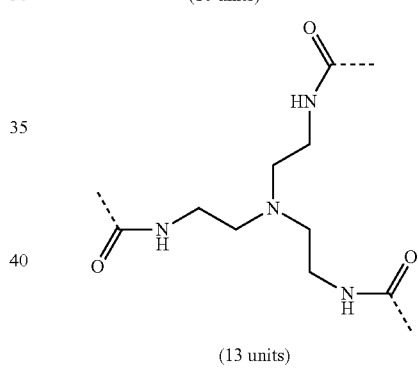

(13 units)

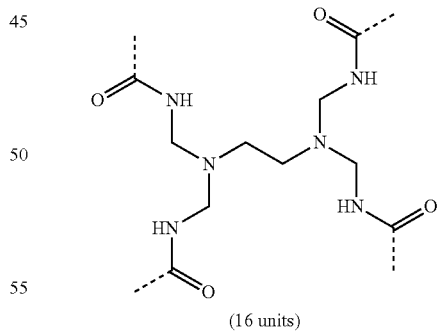

(16 units)

The dotted lines indicate the bondings to the spacergroup S1.

The nature and structure of the spacergroups S1 or S2 is not particularly limited, either.

The spacergroups are comprised of units connected with each other. Typical units include: $CH_3-$, $-CH_2-$, $-O-$, $-S-$, $-NR^1-$, $-CO-$, $-CR^1=$,

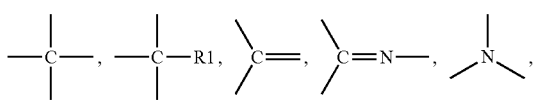

—N=, —CR¹R²—, with R¹ and R² independently selected from hydrogen, alkyl, substituted alkyl, alkenyl, cycloalkyl, substituted cycloalkyl, arylalkyl, aryl or substituted aryl.

These units can form linear, branched or cyclic structures such as alkyl, cycloalkyl, aryl, ester, urethane or amide groups.

The structure of S1 can be identical to the structure of S2. However, in some embodiments the structure of S1 is different from S2. In a specific embodiment the number of units being present in S1 is less or equal than the number of units being present in S2.

In a specific embodiment, S1 may have a saturated hydrocarbon structure.

In another specific embodiment, S2 may have a saturated hydrocarbon structure.

Typical examples of useful spacer groups for S1 include:

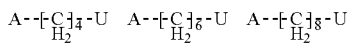

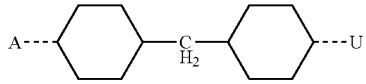

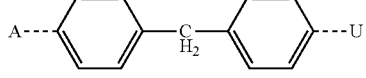

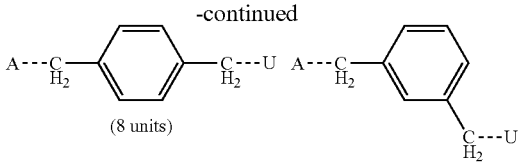

(8 units)

The dotted lines indicate the chemical bonding to either the group A or the group U.

Typical examples of useful spacer groups for S2 include:

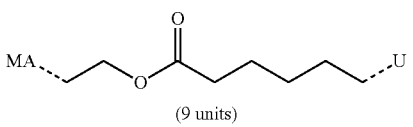

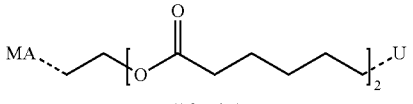

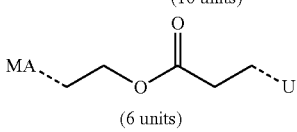

The dotted lines indicate the chemical bonding to either the (meth)acrylate group or the group U. The number of the units to be counted according to the invention is given in brackets.

Specific examples of hardenable component (A1) include

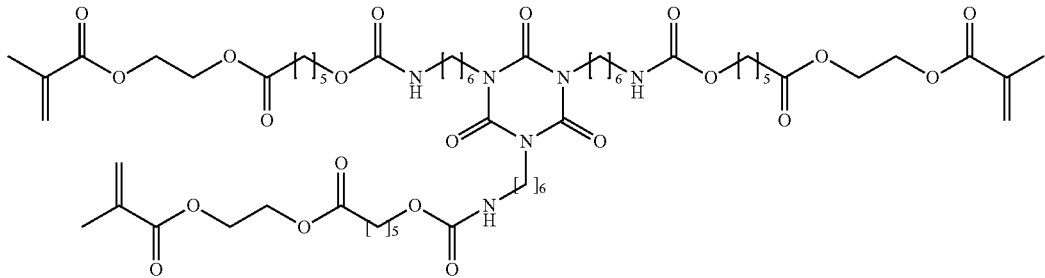

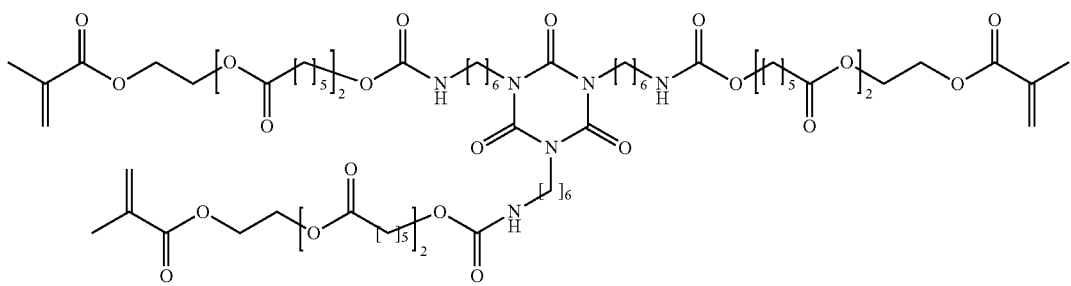

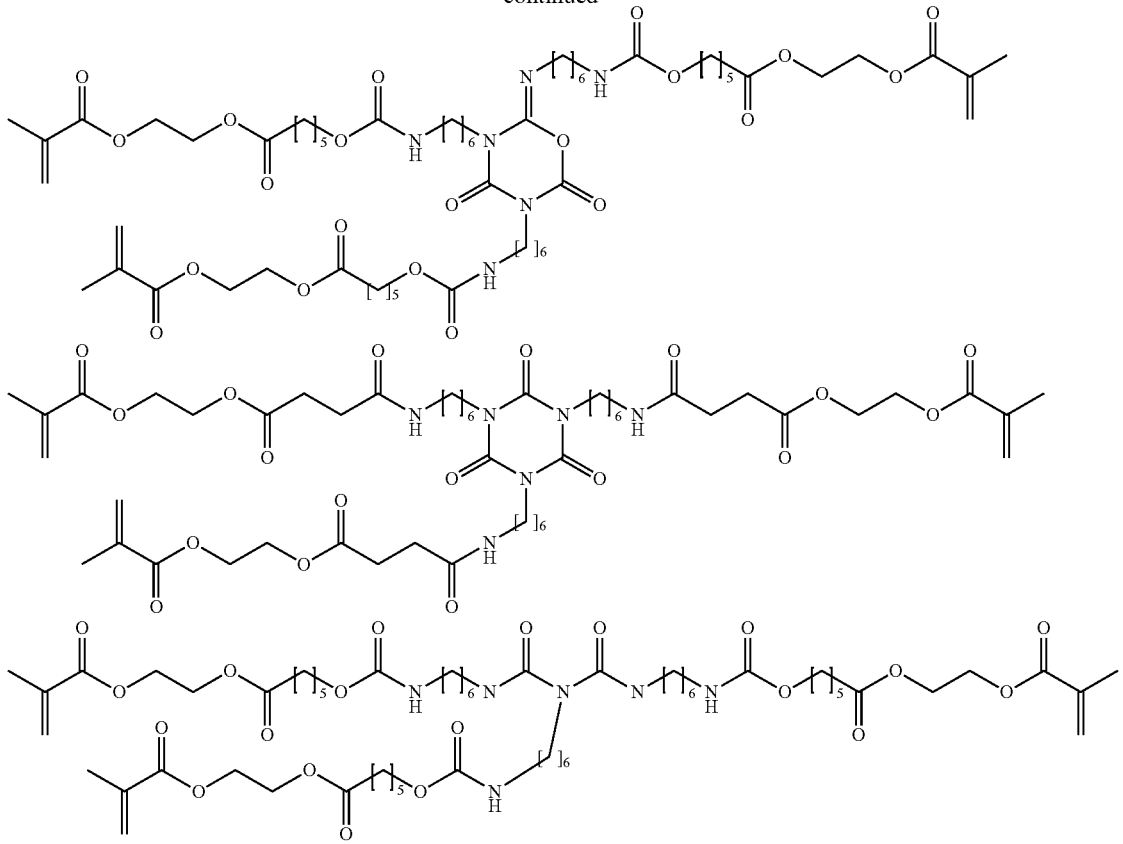

Further suitable urethane(meth)acrylates are based on α,ω-terminated poly(meth)acrylatdiols (e.g. as described in EP 1242493 B1) or can be a polyester, polyether, polybutadiene or polycarbonate urethane(meth)acrylate (e.g. as described in U.S. Pat. No. 6,936,642 B2).

Hardenable component (A1) is typically present in an amount of at least about 1 or at least about 3 or at least about 4.5 wt. % with respect to the weight of the whole composition.

Hardenable component (A1) is typically present in an amount of utmost about 20 or utmost about 15 or utmost about 10 wt. % with respect to the weight of the whole composition.

Thus, hardenable component (A1) is typically present in an amount from about 1 to about 20 or from about 3 to about 15 or from about 4.5 to about 10 wt. % with respect to the weight of the whole composition.

It was found that using a hardenable urethane(meth)acrylate component and more particularly, the components described above, is beneficial to provide the hardended composition with sufficient flexibility and functions as a kind of toughening agent useful to improve the fracture toughness of the cured dental composition.

The dental composition comprises a hardenable component (A2) being a radically polymerizable (meth)acrylate with a functionality of at least 2. The hardenable component (A2) is different from component (A1), e.g. with respect to functionality, chemical moieties, molecular weight or combinations thereof. Hardenable component (A2) does typically not comprise an urethane moiety.

If desired, the dental composition may comprise at least two, three or four different kinds of hardenable component (A2). The molecular weight of hardenable component (A2) is at least about 170 or at least about 200 or at least about 300 g/mol.

The molecular weight of hardenable component (A2) is typically in a range from about 170 to about 3,000 or from about 200 to about 2,500 or from about 300 to about 2,000 g/mol.

The hardenable component (A2) has free radically active functional groups and includes monomers, oligomers, and polymers having two or more ethylenically unsaturated groups.

Such free radically polymerizable materials include di- or poly-acrylates and methacrylates such glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyl-dimethylmethane, bis[1-(3-acryloxy-2-hydroxy)]-p-propoxyphenyl-dimethylmethane; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as diallyl phthalate, divinyl succinate, divinyl adipate and divinylphthalate.

Preferred ethylenically unsaturated monomers are methacrylate and acrylate monomers, such as di(meth)acrylates of propanediol, butanediol, hexanediol, octanediol, nonanediol, decanediol and eicosanediol, di(meth)acrylates of ethylene glycol, of polyethylene glycols and of polypropylene glycols, di(meth)acrylates of ethoxylated bisphenol A, for example 2,2'-bis(4-(meth)acryloxytetraethoxyphenyl)propanes, and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826, such as bis[3[4]-methacryl-oxymethyl-8 (9)-tricyclo[$5.2.1.0^{2,6}$] decylmethyl triglycolate. Particularly suitable are 2,2-bis-4(3-methacryloxy-2-hydroxypropoxy) phenylpropane (Bis-GMA), 2,2-bis-4(3-methacryloxypropoxy)phenylpropane, triethylene glycol dimethacrylate (TEGDMA), and di(meth)acrylates of bishydroxymethyltricyclo-($5.2.1.0^{2,6}$)decane.

It was found that using a hardenable component (A2) and more particularly, the components described above, can be beneficial to provide the hardened composition with sufficient mechanical strength as it may function as a kind of crosslinking agent useful to improve the mechanical properties of the cured dental composition.

Hardenable component (A2) is typically present in an amount of at least about 5 or at least about 10 or at least about 15 wt. % with respect to the weight of the whole composition.

Hardenable component (A2) is typically present in an amount of utmost about 60 or utmost about 50 or utmost about 45 wt. % with respect to the weight of the whole composition.

Thus, hardenable component (A2) is typically present in an amount from about 5 to about 60 or from about 10 to about 50 or from about 15 to about 45 wt. % with respect to the weight of the whole composition. The dental composition described in the present text comprises dark or redox curing initiator components or system.

One class of initiators capable of initiating polymerization of free radically active functional groups includes conventional chemical initiator systems such as a combination of an organic peroxide and an amine. These initiators, which rely upon a redox reaction, are often referred to as "auto-cure catalysts." They are typically supplied as two-part systems in which the reactants (reducing and oxidizing agent) are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. to 150° C. under normal conditions. This procedure is preferred for initiating polymerization of materials occurring outside of the oral environment.

Organic peroxide compounds together with so-called activators are suitable as redox initiator systems. In particular, compounds such as lauroyl peroxide, benzoyl peroxide and p-chlorobenzoyl peroxide and p-methylbenzoyl peroxide can be considered as organic peroxide compounds.

Suitable as activators are, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines, in particular N,N-bis-([beta]-oxybutyl)-3,5-di-t-butylaniline as well as N,N-bis-(hydroxyalkyl)-3,4,5-trimethylaniline.

Well-suited activators are also the barbituric acids and barbituric acid derivatives as described in US 2003/008967, DE 14 95 520 as well as the malonyl sulfamides described in U.S. Pat. No. 4,544,742 (corresponding to EP 0 059 451).

Preferred malonyl sulfamides are 2,6-dimethyl-4-isobutyl-malonyl sulfamide, 2,6-diisobutyl-4-propylmalonyl sulfamide, 2,6-dibutyl4-propylmalonyl sulfamide, 2,6-dimethyl4-ethylmalonyl sulfamide and 2,6-dioctyl4-isobutyl malonyl sulfamide. For further acceleration, the polymerization is preferably carried out in the presence of heavy-metal compounds and ionogenic halogen or pseudohalogen.

The heavy metal is suitably used in the form of soluble organic compounds. Likewise, the halide and pseudohalide ions are suitably used in the form of soluble salts, as examples there can be named the soluble amine hydrochlorides as well as quarternary ammonium chloride compounds. Suitable accelerators are in particular metals from the iron or copper group, preferably copper and iron complexes and in particular copper complexes. The heavy metal is preferably employed in the form of soluble organic compounds. Suitable are, for example, iron carboxylates, copper carboxylates, iron procetonate, copper procetonate, copper naphthenate, copper acetate and iron naphthenate.

Further suitable redox initiating systems are described in G. Misra et al., Prog. Polym. Sci. Vol. 8, pp. 61-131 (1982). For shelf-life reasons the dark curing components of the initiating system require separate storage of oxidizing and reducing agents. Therefore, the dental composition described in the present text is typically provided as two part systems.

Some components of the dark curing system (later referred to as (X)) are contained in the base part or paste of a kit of parts, some components of the dark curing system (later referred to as (Y)) are contained in the catalyst part or paste of a kit of parts.

Typical examples for dark curing initiator component(s) (X)—contained in a base part—include amine hydrochlorides (e.g. dibutylphenylethyl-amine hydrochloride) and copper containing components (e.g. Copper(II) bis(1-phenylpentan-1,3-dione) complex). Typical examples for dark curing initiator component(s) (Y)—contained in a catalyst base part—include: components comprising a barbituric acid moiety (e.g. 1-Benzyl-5-phenyl-barbituric acid) and malonyl sulfamides, peroxides (e.g. tert. Butylperoxy-3,5, 5-trimethylhexanoate).

Besides dark curing initiator component, the dental composition described in the present text may also contain in addition visible light curing initiator components if desired.

Such initiators typically can be capable of generating free radicals for polymerization upon exposure to light energy having a wavelength between about 400 and about 800 nm. Examples of visible light curing initiator components include for example systems based on an amine and an a-diketone. Suitable systems are described e.g. in U.S. Pat. No. 4,071,124 and WO 2009151957. The content of these references is herewith incorporated by reference.

The dental composition may further comprise in addition at least one of or all of the following components:
plasticiser,
x-ray visible particles,
additives.

Adding a plasticiser component is optional.

Plasticisers which can be added typically include components without polymerizable moieties. Examples of useful plasticisers include polyethylene glycol derivatives, polypropylene glycols, dibutyl-, dioctyl-, dinonyl- and diphenyl phthalate, esters from adipinic, sebacinic and citric acid, phosphates such as tricresyl phosphate, paraffin oils, glycerol triacetate, ethoxylated and propoxylated Bisphenol A diacetate and silicone oils and mixtures thereof.

The molecular weight of the plasticiser is typically in a range from about 200 to about 2,500 or from about 300 to about 2,000 g/mol. If present, plasticiser are typically present in an amount from about 0.1 to about 10 or from about 0.5 to about 7.5 or from about 1 to about 5 wt. % with respect to the weight of the whole composition. Using a plasticiser typically may facilitate the formulation of the composition, in particular if the composition should be provided in paste form.

Adding x-ray visible particles to the dental composition is beneficial in that it enables the practitioner to better identify the dental material in the mouth of a patient and distinguish between sound dental tooth structure and the dental restoration material. The dental material becomes radiopaque.

Radio-Opacity of a dental material is advantageous in certain instances where X-rays are used to diagnose a dental condition. For example, a radiopaque material would allow the detection of secondary caries that may have formed in the tooth tissue surrounding a filling. The desired degree of radio-opacity can be varied, depending upon the particular application and the expectations of the practitioner evaluating the X-ray film.

Suitable x-ray visible particles include particles of metal oxides and metal fluorides. Oxides or fluorides of heavy metals having an atomic number greater than about 28 can be preferred. The heavy metal oxide or fluoride should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide or fluoride is an oxide or fluoride of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Suitable metal fluorides are e.g. Yttriumtrifluoride and Ytterbiumtrifluoride. Most preferably, the oxides and fluorides of heavy metals having an atomic number greater than 30, but less than 72 are optionally included in the materials of the invention. Particularly preferred radiopacifying metal oxides include lanthanum oxide, zirconium oxide, yttrium oxide, ytterbium oxide, barium oxide, strontium oxide, cerium oxide, and combinations thereof. Other suitable fillers to increase radiopacity are salts of barium and strontium especially strontium sulphate and barium sulphate. The heavy metal oxide or metal fluoride particles may be surface treated.

The mean particle size of the x-ray visible particles (in non-aggregated state) is typically within a range from about 20 to about 500 or from about 50 to about 300 nm. If present, x-ray visible particles are typically present in an amount from about 0.1 to about 15 or from about 1 to about 10 or from about 2 to about 5 wt.-% with respect to the weight of the whole composition.

Further additives, which can be optionally added, include retarder(s), anti-microbial(s), pigment(s), dyes, photobleachable colorant(s), stabilizer(s) and fluoride releasing materials.

Examples of pigment(s) and dye(s), which can be used include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual colouring of the dental compositions.

Examples of photobleachable colorant(s) which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725. The colour of the compositions of the invention may be additionally imparted by a sensitizing compound.

Examples of fluoride release agent(s) which can be present include naturally occuring or synthetic fluoride minerals. These fluoride sources can optionally be treated with surface treatment agents. Further additives, which can be added, include stabilizer(s), especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers). Such adjuvants may optionally comprise reactive moiety so that they will be copolymerized with the resin.

A suitable retarder is for example 1,2-diphenylethylene. Further additives, which can be added, include absorbers, emulsifiers, antioxidants and wetting agents. There is no absolute need for these adjuvants or additives to be present, so adjuvants or additives might not be present at all. However, if they are present they are typically present in an amount which is not detrimental to the intended purpose.

Useful amounts for additives include:
  at least about 0.1 wt. % or at least about 0.5 wt. % or at least about 1 wt. % and/or
  up to about 15 wt. % or up to about 10 wt. % or up to about 5 wt. %.

Typical ranges include from about 0.1 wt-% to about 15 wt. % or from about from about 0.5 wt. % to about 10 wt. % or from about 1 wt. % to about 5 wt. %.

All components used in the dental composition described in the present text should be sufficiently biocompatible, that is, the composition should not produce a toxic, injurious, or immunological response in living tissue. The composition described in the present text does typically not comprise components selected from
  polymerizable component comprising an acidic group e.g. in an amount above about 5 wt. %,
  monofunctional (meth)acrylates e.g. in an amount above about 5 wt. %,
  solvent e.g. in an amount above about 5 wt. %,
  acid reactive filler e.g. in an amount above about 5 wt. %,
  filler particles having a mean particle size from about 1 to about 100 μm e.g. in an amount above about 10 wt. % or above about 5 wt. %,
  non-agglomerated nano-sized fillers e.g. in an amount above about 10 wt. % or above about 5 wt. %,
and mixtures thereof.

That is, those components are typically not wilfully added and thus are not present in an amount above about 10 or above about 8 or above about 5 or above about 2 wt. % with respect to the weight of the whole composition.

However, depending on the raw materials chosen, it may sometimes be unavoidable that the composition may contain traces of either of the above components.

Examples of acid reactive fillers which are typically not present include fluoroaluminasilicate glasses (sometimes also referred to as GIZ glasses), hydroxides, oxides and carbonates of alkaline earth metals like $Ca(OH)_2$, $Mg(OH)_2$, $CaO$, $MgO$, $CaCO_3$, $MgCO_3$.

Adding filler having a mean particle size in the above mentioned range in an amount above about 10 wt. % may negatively influence properties like polishability and gloss retention.

Examples of such kind of fillers include fluoroaluminosilicate glasses, quartz, ground glasses, non-water-soluble fluorides such as $CaF_2$, cristobalite, calcium silicate, zeolites, including the molecular sieves, metal oxide powders, such as aluminium or zirconia or their mixed oxides, barium sulphate, calcium carbonate. Adding such a filler in a high amount may negatively influence the aesthetic properties of the hardened dental composition.

Examples of solvents which are typically not present include linear, branched or cyclic, saturated or unsaturated alcohols, ketones, esters or mixtures of two or more of said type of solvents with 2 to 10 C atoms, like methanol, ethanol, iso-propanol, n-propanol, THF, acetone, methyl-ethyl ketone, cyclohexanol, toluene, alkanes and acetic acid alkyl esters.

The dental composition described in the present text can contain the components in the following amounts:
  filler (F1): from about 30 to about 70 wt. %, or from about 35 to about 60 wt. %,
  filler (F2): from about 1 to about 20 wt. %, or from about 3 to about 15 wt. %,
  hardenable component (A1): from about 1 to about 20 wt. %, or from about 3 to about 15 wt. %, or from about 4.5 to about 10 wt. %,
  hardenable component (A2): from about 5 to about 60 wt. %, or from about 10 to about 50 wt. %, or from about 15 to about 45 wt. %,
  dark curing initiator components: from about 0.1 to about 5 wt. %, or from about 0.3 to about 4 wt. %, or from about 0.5 to about 3 wt. %,
  plasticiser: from about 0.1 to about 10 wt. %, or from about 0.5 to about 7.5 wt. %, or from about 1 to about 5 wt. %,
  x-ray visible particles: from about 0.1 to about 15 wt. %, or from about 1 to about 10 wt. %, or from about 2 to about 5 wt. %,
  additives: from about 0.1 to about 15 wt. %, or from about 0.5 to about 10 wt. %, or from about 1 to about 5 wt. %,
wt. % with respect to the weight of the whole composition.

The composition described in the present text is typically provided as a two part composition.

One part is typically called the base part, whereas the other part is typically called the catalyst part. Upon combination of the two parts a hardening composition is obtained.

If the individual parts are provided in paste form, the viscosity of the individual pastes is typically in a range from about 1 to about 100 Pa*s or from about 10 to about 75 Pa*s (measured at 23° C.; shear rate 30 1/s using a Physica Rheometer).

Thus, according to a further embodiment, the dental composition is provided as a kit of parts comprising a base part (A) and a catalyst part (B), base part (A) comprising:
  filler (F1) in an amount of from about 30 to about 70 wt. %,
  filler (F2) in an amount from about 1 to about 20 wt. %,
  hardenable component (A1),
  hardenable component (A2),
  dark curing initiator component(s) (X),
  wt. % with respect to the weight of the base part,
catalyst part (B) comprising
  filler (F2),
  dark curing initiator component(s) (Y),
dark curing initiator component(s) (X) and dark curing initiator component(s) (Y) forming a redox-initiator system.

According to a further embodiment, the dental composition described in the present text is described as a kit of parts comprising a base part (A) and a catalyst part (B), base part (A) comprising
  filler (F1) in an amount of from about 30 to about 70 wt. %,
  filler (F2) in an amount from about 1 to about 20 wt. %,
  hardenable component (A1) from about 1 to about 20 wt. %,
  hardenable component (A2) from about 5 to about 60 wt. %,
  dark curing initiator component(s) (X),
  wt. % with respect to the weight of the base part,
and a catalyst part B comprising
  filler (F2) from about 1 to about 20 wt. %,
  dark curing initiator component(s) (Y),
  wt. % with respect to the weight of the catalyst part,
dark curing initiator component(s) (X) and dark curing initiator component(s) (Y) forming a redox-initiator system.

According to a further embodiment, the dental composition is provided as a kit of parts comprising a base part (A) and a catalyst part (B),
base part (A) comprising:
  filler (F1) in an amount of from about 30 to about 70 wt. %,
  filler (F2) in an amount from about 1 to about 20 wt. %,
  hardenable component (A1),
  hardenable component (A2),
  dark curing initiator component(s) (X),
  wt. % with respect to the weight of the base part,
catalyst part (B) comprising:
  filler (F1) in an amount of from about 30 to about 70 wt. %,
  filler (F2) in an amount from about 1 to about 20 wt. %,
  hardenable component (A1),
  hardenable component (A2),
  dark curing initiator component(s) (Y),
  wt. % with respect to the weight of the catalyst part,
dark curing initiator component(s) (X) and dark curing initiator component(s) (Y) forming a redox-initiator system,
neither the base part A nor the catalyst part B comprising any of the following components:
  polymerizable component comprising an acidic group above about 5 wt. %,
  monofunctional (meth)acrylates above 5 wt. %,
  solvent in an amount above about 5 wt. %,
  acid reactive filler above about 5 wt. %,
  filler particles having a mean particle size from about 1 to about 100 μm in an amount above about 10 wt. %.

Besides filler and dark curing initiator component, the catalyst part (B) optionally contains a plasticiser to facilitate the production of a paste. Plasticisers which can be used are described above.

In certain embodiments the dark-curable or redox reaction curable composition fulfils at least one or more, sometimes all of the following parameters:

working time: from about 30 sec to about 1.5 min, or from about 45 sec to about 1 min, setting time: from about 2.5 to about 6 min, or from about 3 to about 5 min, flexural strength after curing: from about 50 to about 200 MPa (measured according to ISO 4049), fracture work after curing from about 5 to about 15 KJ/m$^2$, impact strength after curing from about 5 to 15 KJ/m$^2$ (measured according to ISO 179-1), abrasion after curing: less than about 20 or less than about 15 or less than about 10 mm$^3$ (measured as described in the Example section).

In certain embodiments, the combination of the following features is desirable: high flexural strength, high fracture work and low abrasion. If desired, the features above can be determined as described in the Example section below.

The composition described in the present text can be produced by mixing its respective components. Mixing is typically done by using mechanical equipment including a speed mixer or dissolver available from e.g. Hauschild+Co KG, Germany. The filler components are usually incorporated as powder or particles. If desired, the filler component(s) can be dispersed in a liquid component of the composition first.

In a further aspect, the invention relates to a kit of parts comprising the dental composition described in the present text, provided in paste/paste form and filled into the chambers of a dual chamber cartridge or two individual syringes, and at least one or all of the following parts:

dental impression material,
dental cement,
adhesive.

During use the dual chamber cartridge is typically equipped with a static mixing tip and acts as a means for mixing and delivery. The volume ratio of chamber (I) to chamber (II) is typically within a range of about 1:1 to about 20:1, especially preferred 1:1 to about 10:1. Useful cartridges are described in US 2007/0090079 or U.S. Pat. No. 5,918,772, the disclosure of which is incorporated by reference. Cartridges which can be used are commercially available from SulzerMixpac AG (Switzerland). Useful static mixing tips are described in US 2006/0187752 or in U.S. Pat. No. 5,944,419, the disclosure of which is incorporated by reference. Mixing tips which can be used are commercially available from SulzerMixpac AG (Switzerland).

Due to the chosen formulation the dental composition described in the present text can easily be mixed and delivered from a dual chamber cartridge known in the art using a manually driven gear. Alternatively, but less preferred, the paste/paste composition described in the present text can be provided in two individual syringes and the individual pastes can be be handmixed prior to use. If desired, to determine whether the extrusion forces which need to be applied are in an acceptable range, the following test can be conducted:

A dual chamber cartridge having a volume of 50 ml (volume ratio from 1:1 to 10:1) containing the catalyst and base paste is equipped with a mixing tip (Sulzer Mixpac) and a plunger and then placed in a holder of a universal testing machine (Zwick Z 010) equipped with a 10 kN load cell. A pusher is placed in a way that it exerts a force on the driving plate of the plunger in order to extrude the dental composition. The speed of the pusher is adjusted to 25 mm/min. If a force of >2 N (software textXpert V 8.1) is recorded recording of the data starts. The measurement is finished when the driving plate/pusher has been moved forward in the cartridge by 20 mm total. An extrusion force below about 1000 N or below about 800 N or below about 600 N is considered acceptable. If the extrusion force extends a certain value, the composition cannot be expressed adequately and mixed by using a manually driven automix-system.

Examples of dental impression material(s) which can be used include materials based on alginate(s), polyether technology, addition curable silicone materials (e.g. VPS materials) and condensation curable silicone materials.

Addition curable silicone materials and curable polyether materials are sometimes preferred due to their better performance and higher accuracy.

The dental impression material is typically characterized by at least one, more or all of the following features:

Consistency (according to ISO 4823): 0,1,2,3,

Setting time: within about 15 min after mixing at ambient conditions (e.g. 23° C.), Shore A hardness (according to ISO 4823; 24 h): at least about 20 or at least about 40, Tensile strength (according to DIN 53504): at least about 0.2 MPa or at least about 3.0 MPa, Elongation at break (according to DIN 53504): at least about 30% or at least about 150% or at least about 200%, Recovery from deformation (according to ISO 4823): at least about 90% or at least about 95% or at least about 98%.

Suitable dental impression materials are also described in EP 2 072 029 B1, U.S. Pat. No. 6,677,393, EP1 512 724 B1, U.S. Pat. No. 6,127,449, WO 2008/014224 and U.S. Pat. No. 5,569,691. The content of these references is herewith incorporated by reference. Dental impression materials are commercially available e.g. from 3M ESPE under the brands Impregum™ or Imprint™. Fixing of the hardened dental composition onto the surface of a tooth structure to be restored is typically done by using an adhesive and/or dental cement.

The nature and properties of the adhesive and/or dental cement are not particularly limited, either unless the desired result cannot be achieved. Especially preferred are adhesive and self-adhesive dental resin cements. Adhesive or self-adhesive dental resin cement systems typically include a polymerizable monomer, an acidic component optionally comprising a polymerizable moiety, a filler, optionally a basic filler and a redox initiator system.

Suitable cements are also described in WO 2007/140440 (A2), US 2010/0016466, US 2004/0110864. The content of these references is herewith incorporated by reference. Adhesive and self-adhesive dental resin cements are commercially available e.g. from 3M ESPE under the brands RelyX$^M$ Unicem, or RelyX™ Ultimate.

The dental composition(s) described in the present text is(are) particularly useful as long term or permanent crown and bridge material. The long term crown and bridge material can be placed directly in the mouth and cured (hardened) in situ, or alternatively, may be fabricated into a prosthesis outside the mouth and subsequently adhered in place inside the mouth.

The dental composition(s) can also be used for producing inlay(s), onlay(s), veneer(s) or as bulkfill material. In another aspect, the invention relates to a method of producing a long term or permanent crown or bridge, the method comprising the steps of placing the composition as described in the present text into the moulds of a set dental impression material. The dental impression material can be an alginate, a silicone (VPS) or polyether impression dental material.

Commercially available alginate impression materials include Palgat™ (3M ESPE). Commercially available silicone impression materials include Express™, Imprint™ and Position™ (3M ESPE). Commercially available polyether impression materials include Impregum™ (3M ESPE).

A typical process in the dental practice comprises one or more steps of:
a) making an impression of hard tooth structure to be restored using a dental impression material, thereby obtaining a negative mould of the tooth structure,
b) waiting until the dental impression material is set,
c) removing the set dental impression material from the hard tooth structure,
d) placing the curable composition described in the present text into the negative mould of the dental impression material,
e) repositioning the filled negative mould onto tooth structure to be restored,
f) waiting until the curable composition is at least partially cured, so that the composition can be removed from the tooth structure to be restored without leaving residues of the composition on the prepared or shaped tooth structure,
g) removing the cured composition from the set impression material,
h) adhesively fixing the removed composition onto the tooth structure to be restored using a dental cement.

The complete disclosures of the patents, patent documents, and publications cited herein are incorporated by reference in their entirety as if each were individually incorporated.

The following examples are given to illustrate the invention.

EXAMPLES

Unless otherwise indicated, all parts and percentages are on a weight basis, all water is de-ionized water and all molecular weights are weight average molecular weight. Moreover, unless otherwise indicated all experiments were conducted at ambient conditions (23° C.; 1013 mbar).
Measurements
Flexural Strength and Fracture Work Flexural strength was determined by conducting a three point flexural strength test according to ISO 4049 using test specimen having the size 2*2*25 mm. Based on the data obtained, the fracture work can be calculated. Fracture work is given in [kJ/m$^2$]. Flexural strength is given in [MPa].
Abrasion Abrasion [mm$^3$] was measured as follows:

Abrasion tests were performed at specific specimens with a slope of 30°. For that purpose the materials were filled into the depression of M12 Inbus-screws and cured according to the manufacturers' instructions.

The specimens were flat grinded using a 75 μm diamond saw and stored in distilled water for 4 days at 36° C. Then chewing simulation was started applying the following conditions:

Chewing force: 80 N; Lateral movement: 4 mm; Sliding movement: 10 mm;
Antagonist: steatite ball; Number of chewing cycles: 1,200,000; Thermocycles (5/55° C.): 5,000.

After conducting the chewing simulation abrasion was determined by measuring the loss of volume using a laser scanning microscope VK-X200(Keyence Company).

Further information about the abrasion test can be found in M. Rosentritt et al., Materialprüfung 39 (1997), p. 77-80.

Compositions

Abbreviations

TABLE 1

| Name | Description | Availability |
|---|---|---|
| Silica nanofiller | Non agglomerated silanized silica nanofiller (50 nm) | Produced according to procedures described in U.S. Pat. No. 6,899,948 B2 |
| HDK H-2000 | Silane treated fumed silica (agglomerated nanoparticles; filler (F2)) | Wacker |
| Aerosil R 711 | Fumed silica (agglomerated nanoparticles; filler (F2)) | Evonik Degussa GmbH |
| Zr/Si Nanocluster | (aggregated nanoparticles; filler (F1)) | Synthesis see below |
| SG-YBF100 | Ytterbium fluoride powder | |
| Cu-procetonate | Copper(II) bis(1-phenylpentan-1,3-dione) complex | |
| Ionol | 2,6-ditert.butyl-4-methylphenol | |
| BZPBS | 1-Benzyl-5-phenyl-barbituric acid | |
| TBPIN | tert. Butylperoxy-3,5,5-trimethylhexanoate | |
| Amine-HCl | dibutylphenylethyl-amine hydrochloride | |
| Z-Acetate | ethoxylated Bisphenol A diacetate | |
| D-Zethacrylate | ethoxylated Bisphenol A dimethacrylate | |
| DESMA | urethane(meth)acrylate | cf. Example 1 of EP 2 167 013 B1 (page 20) |
| Plex 6661 | 7,7,9-trimethyl-4,13-dioxo-3,14-dioxa-5,12-diazahexadecane-1,16-dioxy-dimethacrylate | |
| TEGDMA | Triethylenglycoldimethacrylate | |
| GDMA | Glyceroldimethacrylate | |
| BPO | Benzoylperoxide | |
| DHEPT | Dihydroxy-para-toluidine | |

Typical Synthesis of Aggregated Filler (F1):

The Zr/Si Nanocluster filler was produced as described in U.S. Pat. No. 6,730,156 B1, column 25, Preparatory Example A. The obtained filler particles were surface treated according to a process as described in Preparatory Example B of U.S. Pat. No. 6,730,156 B1.

General Process for Producing the Dental Composition(s)

The respective components were mixed using a speed mixer (Hausschild). The base paste and catalyst paste were filled in a dual chamber cartridge (SulzerMixpac). On the cartridge a static mixing tip (SulzerMixpac) was mounted and the composition dispensed by using a manually driven gear. The mixing ratio of base paste to catalyst paste was 10:1 for Examples 1 and 2 and Comparative Examples 1-3 and 1:1 for Example 3. The cured pastes were analyzed with respect to their properties. The results are given in Table 8.

Example 1

TABLE 2

| Component | Paste A Weight % | Component | Paste B Weight % |
|---|---|---|---|
| Zr/Si Nanocluster | 42.5 | HDK H-2000 | 10.0 |
| Aerosil R 711 | 2.0 | Z-Acetate | 79.7 |
| SG-YBF100 | 2.5 | BZPBS | 10.0 |
| HDK H-2000 | 4.0 | TBPIN | 0.3 |

TABLE 2-continued

| Component | Paste A Weight % | Component | Paste B Weight % |
|---|---|---|---|
| D-Zethacrylate | 43.964 | | |
| DESMA | 4.813 | | |
| Copper-procetonate | 0.003 | | |
| Amine-HCl | 0.19 | | |
| Ionol | 0.03 | | |
| Total: | 100 | Total | 100 |

Comparative Example 1

(Use of Non Agglomerated Nanofillers)

TABLE 3

| Component | Paste A Weight % | Component | Paste B Weight % |
|---|---|---|---|
| Silica nanofiller | 24.0 | HDK H-2000 | 10.0 |
| HDK H-2000 | 8.7 | Z-Acetate | 79.7 |
| D-Zethacrylate | 53.677 | BZPBS | 10.0 |
| DESMA | 13.4 | TBPIN | 0.3 |
| Cu-procetonate | 0.003 | | |
| Amine-HCl | 0.19 | | |
| Ionol | 0.03 | | |
| Total: | 100 | Total | 100 |

Comparative Example 2

(Use of Non-Agglomerated Nanoparticles in an Increased Amount Compared to Comparative Example 1)

TABLE 4

| Component | Paste A Weight % | Component | Paste B Weight % |
|---|---|---|---|
| Silica nanofiller | 42.5 | HDK H-2000 | 10.0 |
| HDK H-2000 | 8.5 | Z-Acetate | 79.7 |
| D-Zethacrylate | 43.977 | BZPBS | 10.0 |
| DESMA | 4.8 | TBPIN | 0.3 |
| Cu-procetonate | 0.003 | | |
| Amine-HCl | 0.19 | | |
| Ionol | 0.03 | | |
| Total: | 100 | Total | 100 |

Example 2

TABLE 5

| Component | Paste A Weight % | Component | Paste B Weight % |
|---|---|---|---|
| Zr/Si Nanocluster | 42.5 | HDK H-2000 | 10.0 |
| Aerosil R 711 | 2.0 | Z-Acetate | 79.7 |
| SG-YBF100 | 2.5 | BZPBS | 10.0 |
| HDK H-2000 | 4.0 | TBPIN | 0.3 |
| D-Zethacrylate | 43.964 | | |
| Plex 6661 | 4.813 | | |
| Copper-procetonate | 0.003 | | |
| Amine-HCl | 0.19 | | |
| Ionol | 0.03 | | |
| Total: | 100 | Total | 100 |

Comparative Example 3

(Formulation Free of Urethane(Meth)Acrylate)

TABLE 6

| Component | Paste A Weight % | Component | Paste B Weight % |
|---|---|---|---|
| Zr/Si Nanocluster | 42.5 | HDK H-2000 | 10.0 |
| Aerosil R 711 | 2.0 | Z-Acetate | 79.7 |
| SG-YBF100 | 2.5 | BZPBS | 10.0 |
| HDK H-2000 | 4.0 | TBPIN | 0.3 |
| D-Zethacrylate | 10.0 | | |
| TEGDMA | 38.777 | | |
| Copper-procetonate | 0.003 | | |
| Amine-HCl | 0.19 | | |
| Ionol | 0.03 | | |
| Total: | 100 | Total | 100 |

Example 3

(1:1 Formulation)

TABLE 7

| Component | Paste A Weight % | Component | Paste B Weight % |
|---|---|---|---|
| Zr/Si Nanocluster | 42.5 | Zr/Si Nanocluster | 42.5 |
| Aerosil R 711 | 1.0 | Aerosil R 711 | 1.0 |
| SG-YBF100 | 2.5 | SG-YBF100 | 2.5 |
| HDK H-2000 | 4.0 | HDK H-2000 | 4.0 |
| GDMA | 29.7 | GDMA | 29.0 |
| DESMA | 19.0 | DESMA | 19.0 |
| BPO | 1.3 | DHEPT | 2.0 |
| Total: | 100 | Total | 100 |

TABLE 8

| | Example 1 | Example 2 | Example 3 | Comparative Example 1 | Comparative Example 2 | Comparative Example 3 |
|---|---|---|---|---|---|---|
| Flexural Strength [MPa] | 99.0 | 111.2 | 144.4 | 78.4 | Not measurable | 79.8 |
| Fracture Work [KJ/m$^2$] | 7.9 | 9.4 | 6.5 | 10.4 | Not measurable | 4.2 |
| Abrasion [mm$^3$] | 8.3 | 9.6 | 6.9 | 33.9 | Not measurable | Not determined |

Results:

Examples 1-3 showed high values in flexural strength and fracture work combined with low abrasion. The use of non agglomerated nanofillers in Comparative Example 1 also resulted in high fracture work but poor abrasion performance due to limited filler loading. The increase of non agglomerated nanofillers in Comparative Example 2 resulted in a formulation which in contrast to Examples 1-3 could not be dispensed and mixed anymore with a static mixer. Comparative Example 3 without urethane (meth) acrylate showed low mechanical properties and a low value in fracture work indicating a certain brittleness.

The invention claimed is:

1. Dental composition comprising:
    filler (F1) comprising aggregated nano-sized particles in an amount of from about 30 to about 70 wt. %,
    filler (F2) comprising agglomerated nano-sized particles in an amount from about 1 to about 20 wt. %,
    hardenable component (A1) being an urethane(meth) acrylate with a functionality of at least 2 and having a molecular weight from about 400 to about 3,000 g/mol,
    hardenable component (A2) being a radically polymerizable (meth)acrylate with functionality of at least 2 being different from component (A1),
    redox curing initiator system,
the dental composition not comprising non-agglomerated nano-sized filler in an amount above about 10 wt. %, wt. % with respect to the weight of the whole composition;
    the hardenable component (A1) being selected from:
        compounds having the structure A-(-S1-U-S2-MA)$_n$
        A being a connector element comprising at least one unit,
        S1 being a spacergroup comprising at least 4 units connected with each other,
        S2 being a spacergroup comprising at least 4 units connected with each other,
        U being a urethane connecting spacergroups S1 and S2,
        MA being an acrylate or methacrylate group,
        n being 3 to 6,
        the units of A, S1 and S2 being independently selected from $CH_3-$, $-CH_2-$, $-O-$, $-S-$, $-NR^1-$, $-CO-$, $-CR^1=$,

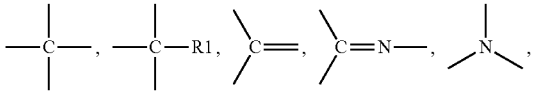

$-N=$,
        $-CR^1R^2-$,
        with $R^1$ and $R^2$ independently selected from hydrogen, alkyl, substituted alkyl, alkenyl, cycloalkyl, substituted cycloalkyl, arylalkyl, aryl or substituted aryl, wherein these units can form linear, branched or cyclic structures,
        and mixtures thereof.

2. Dental composition of claim 1, wherein filler (F1) has at least one or all of the following features:
    Specific surface: from about 50 to about 400 m$^2$/g,
    comprising particles selected from $SiO_2$, $ZrO_2$ and mixtures thereof.

3. Dental composition of claim 1, filler (F2) has at least one or all of the following features:
    Specific surface: from about 30 to about 400 m$^2$/g,
    comprising particles selected from $SiO_2$, $ZrO_2$, $Al_2O_3$ and mixtures thereof.

4. Dental composition of claim 1, the hardenable component (A2) being selected from glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyl-dimethylmethane, bis[1-(3-acryloxy-2-hydroxy)]-p-propoxyphenyldimethylmethane, bis-acrylates and di(meth) acrylates of ethylene glycol, of polyethylene glycols and of polypropylene glycols of molecular weight 200-500, di(meth)acrylates of ethoxylated bisphenol A, 2,2'-bis(4-(meth)acryloxytetraethoxyphenyl)propanes, bis[3[4]-methacryloxymethyl -8(9)-tricyclo[5.2.1.0$^{2,6}$]decylmethyl triglycolate, 2,2-bis-4-(3-methacryloxypropoxy)phenylpropane, di(meth)acrylates of bishydroxymethyltricyclo-(5.2.1.0$^{2,6}$)decane and mixtures thereof.

5. The dental composition of claim 1, the redox curing initiator system comprising components being selected from peroxide(s), components comprising a barbituric acid moiety, malonyl sulfamide(s) and mixtures thereof.

6. The dental composition of claim 1, further comprising at least one of or all of the following components:
    plasticiser,
    x-ray visible particles,
    pigments,
    additives selected from retarder(s), anti-microbial(s), stabilizer(s), fluoride releasing material(s), absorber(s), emulsifier(s), antioxidant(s) and wetting agent(s), dye(s) and mixtures thereof.

7. The dental composition of claim 1 comprising a plasticiser selected from component(s) containing a polyethylene glycol moiety, polypropylene glycol(s), dibutyl-, dioctyl-, dinonyl- and diphenyl phthalate(s), ester(s) from adipinic, sebacinic and citric acid, paraffin oil(s), glycerol triacetate, ethoxylated and propoxylated Bisphenol A diacetate and silicone oil(s) and mixtures thereof.

8. The dental composition of claim 1, wherein the dental composition has at least one or all of the following parameters:
    working time: from about 30 sec to about 1.5 min,
    setting time: from about 2.5 to about 6 min,
    flexural strength after curing: from about 50 to about 200 MPa measured according to ISO 4049,
    fracture work after curing: from about 5 to about 15 KJ/m$^2$,
    impact strength after curing: from about 5 to 15 KJ/m$^2$ measured according to ISO 179-1,
    abrasion after curing: less than about 20 mm$^3$.

9. The dental composition of claim 1 not comprising at least one of or all of the following components:
    polymerizable component comprising an acidic group in an amount above about 5 wt. %,
    monofunctional (meth)acrylates in an amount above about 5 wt. %,
    solvent in an amount above about 5 wt. %,
    acid reactive filler in an amount above about 5 wt. %,
    filler particles having a mean particle size from about 1 to about 100 µm in an amount above about 10 wt. %.

10. The dental composition of claim 1, wherein:
amount of filler (F1): from about 30 to about 70 wt. %,
amount of filler (F2): from about 1 to about 20 wt. %,
amount of hardenable component (A1): from about 1 to about 20 wt. %,
amount of hardenable component (A2): from about 5 to about 60 wt. %, wt. % with respect to the weight of the whole composition.

11. The dental composition of claim 1 being provided as a kit of parts comprising a base part (A) and a catalyst part (B),
base part (A) comprising:
filler (F1) in an amount of from about 30 to about 70 wt. %,
filler (F2) in an amount from about 1 to about 20 wt. %,
hardenable component (A1),
hardenable component (A2),
dark curing initiator component(s) (X),
wt. % with respect to the weight of the base part,
catalyst part (B) comprising
filler (F2),
dark curing initiator component(s) (Y),
the dark curing initiator component(s) (X) and dark curing initiator component(s) (Y) forming a redox-initiator system.

12. The dental composition of claim 1 being provided as a kit of parts comprising a base part (A) and a catalyst part (B),
base part (A) comprising:
filler (F1) in an amount of from about 30 to about 70 wt. %,
filler (F2) in an amount from about 1 to about 20 wt. %,
hardenable component (A1) in an amount from about 1 to about 20 wt. %,
hardenable component (A2) in an amount from about 5 to about 60 wt. %,
dark curing initiator component(s) (X),
wt. % with respect to the weight of the base part,
a catalyst part (B) comprising:
filler (F1) in an amount of from about 30 to about 70 wt. %,
filler (F2) in an amount from about 1 to about 20 wt. %,
dark curing initiator component(s) (Y),
wt. % with respect to the weight of the catalyst part,
dark curing initiator component(s) (X) and dark curing initiator component(s) (Y) forming a redox-initiator system,
neither the base part (A) nor the catalyst part (B) comprising any of the following components:
polymerizable component comprising an acidic group above about 5 wt. %,
monofunctional (meth)acrylates above 5 wt. %,
solvent in an amount above about 5 wt. %,
acid reactive filler above about 5 wt. %,
filler particles having a mean particle size from about 1 to about 100 μm in an amount above about 10 wt. %,
non-agglomerated nano-sized fillers in an amount above about 10 wt. %.

13. A kit of parts of claim 11 further including at least or all of the following parts:
dental impression material,
dental cement,
adhesive.

14. A method of preparing a dental article comprising:
providing a dental composition according to claim 1; and
hardening the composition to produce a dental article selected from the group consisting of crown(s), bridge(s), inlay(s), onlay(s), veneer(s) and bulkfill material.

15. A kit of parts of claim 12 comprising at least or all of the following parts:
dental impression material,
dental cement,
adhesive.

16. The dental composition of claim 1, wherein $R^1$ and $R^2$ are each independently selected from the group consisting of alkyl, cycloalkyl, aryl, ester, urethane, and amide groups.

* * * * *

UNITED STATES PATENT AND TRADEMARK OFFICE
CERTIFICATE OF CORRECTION

PATENT NO. : 9,782,329 B2
APPLICATION NO. : 14/902948
DATED : October 10, 2017
INVENTOR(S) : Reinhold Hecht et al.

It is certified that error appears in the above-identified patent and that said Letters Patent is hereby corrected as shown below:

In the Specification

Column 3
Line 21, delete "i. e.," and insert -- i.e., --, therefor.

Column 3
Line 22, delete "i. e.," and insert -- i.e., --, therefor.

Column 4
Line 51, after "thereof" insert -- . --.

Column 8
Line 25, delete "Pycometer (Micrometrics," and insert -- Pycnometer (Micromeritics, --, therefor.

Column 8
Line 53, after "kinds" insert -- . --.

Column 9
Line 40, delete "γ-methacryloxylpropyltrimethoxysilane," and insert
-- γ-methacryloxypropyltrimethoxysilane, --, therefor.

Column 10
Line 32, delete "hardended" and insert -- hardened --, therefor.

Column 11
Line 4, delete "diisocycanate," and insert -- diisocyanate, --, therefor.

Column 11
Lines 4-5, delete "diisocycanate," and insert -- diisocyanate, --, therefor.

Signed and Sealed this
Twenty-ninth Day of May, 2018

Andrei Iancu
*Director of the United States Patent and Trademark Office*

Column 11
Line 5, delete "diisocycanate," and insert -- diisocyanate, --, therefor.

Column 11
Line 6, delete "diisocycanate," and insert -- diisocyanate, --, therefor.

Column 11
Line 7, delete "diisocycanate," and insert -- diisocyanate, --, therefor.

Column 11
Line 37, delete "tetrahydrofurane," and insert -- tetrahydrofuran, --, therefor.

Column 11
Line 48 (approx.), delete "bezene" and insert -- benzene --, therefor.

Column 13
Line 9 (approx.), delete "(1 units)" and insert -- (1 unit) --, therefor.

Column 20
Line 12 (approx.), delete "quarternary" and insert -- quaternary --, therefor.

Column 20
Line 51, delete "a-diketone." and insert -- α-diketone. --, therefor.

Column 21
Line 64, delete "Neazopon" and insert -- Neozapon --, therefor.

Column 23
Line 5, delete "fluoroaluminasilicate" and insert -- fluoroaluminosilicate --, therefor.

Column 25
Line 54, delete "be be" and insert -- be --, therefor.

Column 28
Line 27, delete "Zethacrylate" and insert -- Methacrylate --, therefor.

Column 28
Line 33 (approx.), delete "Triethylenglycoldimethacrylate" and insert
-- Triethyleneglycoldimethacrylate --, therefor.